United States Patent
Araki et al.

(10) Patent No.: US 11,066,343 B2
(45) Date of Patent: Jul. 20, 2021

(54) METHOD FOR PRODUCING P-XYLENE

(71) Applicant: ENEOS Corporation, Tokyo (JP)

(72) Inventors: Yasuhiro Araki, Tokyo (JP); Mayumi Yokoi, Tokyo (JP); Ryoji Ida, Tokyo (JP); Atsushi Segawa, Tokyo (JP); Masanari Akiyama, Tokyo (JP)

(73) Assignee: ENEOS CORPORATION, Tokyo (JP)

( * ) Notice: Subject to any disclaimer, the term of this patent is extended or adjusted under 35 U.S.C. 154(b) by 0 days.

(21) Appl. No.: 16/349,394

(22) PCT Filed: Nov. 16, 2017

(86) PCT No.: PCT/JP2017/041251
§ 371 (c)(1),
(2) Date: May 13, 2019

(87) PCT Pub. No.: WO2018/092840
PCT Pub. Date: May 24, 2018

(65) Prior Publication Data
US 2019/0263731 A1 Aug. 29, 2019

(30) Foreign Application Priority Data
Nov. 16, 2016 (JP) .............................. JP2016-223197

(51) Int. Cl.
| | |
|---|---|
| *C07C 2/24* | (2006.01) |
| *C07C 5/32* | (2006.01) |
| *B01J 21/04* | (2006.01) |
| *B01J 23/00* | (2006.01) |
| *B01J 23/02* | (2006.01) |
| *B01J 23/26* | (2006.01) |
| *B01J 23/62* | (2006.01) |
| *C07C 5/25* | (2006.01) |
| *C07C 5/333* | (2006.01) |
| *C07C 5/41* | (2006.01) |
| *C07C 2/28* | (2006.01) |
| *C07B 61/00* | (2006.01) |

(52) U.S. Cl.
CPC .............. *C07C 2/24* (2013.01); *B01J 21/04* (2013.01); *B01J 23/005* (2013.01); *B01J 23/02* (2013.01); *B01J 23/26* (2013.01); *B01J 23/62* (2013.01); *B01J 23/626* (2013.01); *C07C 2/28* (2013.01); *C07C 5/2506* (2013.01); *C07C 5/333* (2013.01); *C07C 5/415* (2013.01); *C07C 5/417* (2013.01); *C07B 61/00* (2013.01); *C07C 2521/04* (2013.01); *C07C 2521/10* (2013.01); *C07C 2521/12* (2013.01); *C07C 2523/26* (2013.01); *C07C 2523/42* (2013.01); *C07C 2523/62* (2013.01); *Y02P 20/52* (2015.11)

(58) Field of Classification Search
None
See application file for complete search history.

(56) References Cited

U.S. PATENT DOCUMENTS

| | | | | |
|---|---|---|---|---|
| 4,169,865 | A * | 10/1979 | Bamforth ................. | C07C 2/84 585/314 |
| 6,177,601 | B1 * | 1/2001 | Bogdan .................. | C07C 5/417 208/138 |
| 7,439,409 | B1 * | 10/2008 | Jan ............................ | C07C 5/31 585/251 |
| 2007/0060779 | A1 * | 3/2007 | Bogdan ................. | B01J 29/405 585/482 |
| 2007/0167662 | A1 * | 7/2007 | Duplan .................... | C07C 4/06 585/653 |
| 2008/0312482 | A1 * | 12/2008 | Jan .......................... | C07C 5/417 585/418 |
| 2011/0040134 | A1 * | 2/2011 | Arnold ................. | C07C 5/2506 585/315 |
| 2011/0087000 | A1 * | 4/2011 | Peters ...................... | C07C 2/12 528/308.3 |
| 2013/0331613 | A1 * | 12/2013 | Kim ........................ | C07C 41/06 568/619 |
| 2014/0128652 | A1 * | 5/2014 | Yamakawa ............... | C07C 2/12 585/510 |

(Continued)

FOREIGN PATENT DOCUMENTS

| | | |
|---|---|---|
| CN | 102596866 | 7/2012 |
| CN | 104447176 | 3/2015 |
| GB | 1598809 | 9/1981 |

(Continued)

OTHER PUBLICATIONS

Nobuhiro Kimura, "Selective Dimerization Process for C4 Fraction", The Japan Petroleum Institute, 2011, pp. 317-321 w/ Eng translation.
International Search Report issued in International Patent Application No. PCT/JP2017/041251, dated Jan. 30, 2018.
International Preliminary Report on Patentability issued in International Patent Application No. PCT/JP2017/041251, dated May 31, 2019.
Office Action issued in JP Patent Application No. 2016-223197, dated Feb. 12, 2020.

(Continued)

*Primary Examiner* — Philip Y Louie
(74) *Attorney, Agent, or Firm* — Greenblum & Bernstein, P.L.C.

(57) ABSTRACT

Provided is a method for producing p-xylene, comprising: a provision step of providing a C4 fraction comprising at least isobutene as a product formed by fluidized catalytic cracking of a heavy oil fraction; a dimerization step of bringing a first raw material comprising the isobutene into contact with a dimerization catalyst to produce a C8 component comprising a dimer of isobutene; and a cyclization step of bringing a second raw material comprising the C8 component with a dehydrogenation catalyst to produce p-xylene through a cyclization/dehydrogenation reaction of the C8 component.

12 Claims, No Drawings

(56) References Cited

U.S. PATENT DOCUMENTS

2015/0274613 A1* 10/2015 Pham .................. C07C 2/58
585/321

FOREIGN PATENT DOCUMENTS

| JP | 31-003423 | 5/1956 |
|----|-----------|--------|
| JP | 50-013780 | 5/1975 |
| JP | 54-009231 | 1/1979 |
| JP | 61-130241 | 6/1986 |
| JP | 08-502478 | 3/1996 |
| JP | 11-253808 | 9/1999 |
| JP | 2009-541458 | 11/2009 |
| JP | 2010-280653 | 12/2010 |
| JP | 2013-010717 | 1/2013 |
| JP | 2013-502414 | 1/2013 |
| JP | 2013-506717 | 2/2013 |
| JP | 2014-513672 | 6/2014 |
| JP | 2015-509046 | 3/2015 |
| JP | 2016-175888 | 10/2016 |
| WO | 94-008920 | 4/1994 |
| WO | 2008-003700 | 1/2008 |
| WO | 2011-044243 | 4/2011 |
| WO | 2013-108979 | 7/2013 |
| WO | 2014/070733 | 5/2014 |

OTHER PUBLICATIONS

Notice of Reasons for Rejection issued in JP Patent App. No. 2016-223197 dated Jun. 2, 2020.
Office Action issued in CN Patent Application No. 201780071051.5, dated Apr. 30, 2021, (includes X, Y, A correspondence table).
Jin Yang, "Production Technology of Basic Organic Raw Materials", China University of Petroleum Press, Sep. 30, 1994; partial English translation.
Rixin Xu, "Elementary Petrochemical Industry", Petroleum Industry Press, Aug. 31, 1983; partial English translation.
Shixiong Lin, "Petroleum Refining Engineering", Petroleum Industry Press, Third Edition, Jul. 31, 2000; partial English translation.
"Synthetic Rubber Industry", Lanzhou Research Institute of Chemical Industry, Fuel Chemical Industry Press, Jul. 31, 1972; partial English translation.

* cited by examiner

METHOD FOR PRODUCING P-XYLENE

TECHNICAL FIELD

The present invention relates to a method for producing p-xylene.

BACKGROUND ART

Examples of various products formed by fluidized catalytic cracking (FCC) of heavy oil fraction include a C4 fraction mainly composed of hydrocarbons having 4 carbon atoms. As an effective method of using the C4 fraction, for example, Patent Literature 1 discloses that FCC-C4 can be used as raw material in production of butadiene. The description in Patent Literature 1 is, however, only an exemplification of raw material, and no specific example with use of the C4 fraction, etc. is described.

CITATION LIST

Patent Literature

Patent Literature 1: Japanese Unexamined Patent Publication No. 2010-280653

SUMMARY OF INVENTION

Technical Problem

An object of the present invention is to provide, as a novel use of a C4 fraction produced by fluidized catalytic cracking of a heavy oil fraction, a method for producing p-xylene from the C4 fraction as a raw material.

Solution to Problem

An aspect of the present invention relates to a method for producing p-xylene, comprising: a provision step of providing a C4 fraction comprising at least isobutene as a product formed by fluidized catalytic cracking of heavy oil fraction; a dimerization step of bringing a first raw material comprising the isobutene into contact with a dimerization catalyst to produce a C8 component comprising a dimer of isobutene; and a cyclization step of bringing a second raw material comprising the C8 component with a dehydrogenation catalyst to produce p-xylene through a cyclization/dehydrogenation reaction of the C8 component.

In an aspect, the C4 fraction may further comprise isobutane, normal butene and normal butane.

The production method according to an aspect may further comprise a separation step of obtaining a fraction (A) comprising isobutene and isobutane and a fraction (B) comprising normal butene and normal butane from the C4 fraction.

In an aspect, the first raw material may comprise the fraction (A).

The production method according to an aspect may further comprise a second separation step of obtaining a fraction comprising isobutene (A-1) and a fraction comprising isobutane (A-2) from the fraction (A).

In an aspect, the first raw material may comprise the fraction (A-1).

The production method according to an aspect may further comprise a butadiene production step of bringing a third raw material comprising the fraction (B) into contact with a dehydrogenation catalyst to produce butadiene.

The production method according to an aspect may further comprise an isomerization step of bringing a third raw material comprising the fraction (B) into contact with an isomerization catalyst to produce isobutene and isobutane.

In an aspect, the isobutene obtained in the isomerization step may be used as a part of the first raw material.

In an aspect, the dimerization catalyst may comprise at least one acidic catalyst selected from the group consisting of sulfuric acid, zeolite, solid phosphoric acid, hydrofluoric acid, an ionic liquid, and an ion exchange resin.

In an aspect, the dehydrogenation catalyst used in the cyclization step may comprise an inorganic oxide support comprising Al and Mg, and an active metal supported on the inorganic oxide support.

In an aspect, the active metal may comprise Pt and Sn.

Advantageous Effects of Invention

According to the present invention, as a novel use of a C4 fraction produced by fluidized catalytic cracking of a heavy oil fraction, a method for producing p-xylene from the C4 fraction as a raw material is provided.

DESCRIPTION OF EMBODIMENTS

Preferred embodiments of the present invention are described as follows.

The method for producing p-xylene according to the present embodiment comprises a provision step of providing a C4 fraction comprising at least isobutene as a product formed by fluidized catalytic cracking (FCC) of heavy oil fraction, a dimerization step of bringing a first raw material comprising the isobutene into contact with a dimerization catalyst to produce a C8 component comprising a dimer of isobutene, and a cyclization step of bringing a second raw material comprising the C8 component into contact with a dehydrogenation catalyst to produce p-xylene through a cyclization/dehydrogenation reaction of the C8 component.

The production method according to the present embodiment enables p-xylene serving as a useful chemical to be efficiently produced from a C4 fraction produced by FCC, providing a novel use of the C4 fraction formed by FCC.

Each of the steps of the production method according to the present embodiment is described in detail as follows.

(Provision Step)

In the provision step, a C4 fraction comprising at least isobutene as a product formed by fluidized catalytic cracking of a heavy oil fraction, is provided. The C4 fraction may comprise, for example, a C4 fraction obtained by distilling crude oil and a C4 fraction derived from a product formed by thermal decomposition of heavy oil fraction or naphtha.

The C4 fraction is a fraction comprising hydrocarbons having 4 carbon atoms as main components (for example, 80 mass % or more, preferably 95 mass % or more), and may further contain isobutane, normal butene and normal butane as the hydrocarbons other than isobutene. Also, the C4 fraction may further contain other hydrocarbons such as butadiene.

The C4 fraction may contain sulfur components. The sulfur content may be, for example, 10000 ppm by mass or less, or may be 100 ppm by mass or less.

The heavy oil fraction as raw material in fluidized catalytic cracking is not particularly limited, and examples thereof include an indirectly desulfurized light oil obtained from a unit for indirectly desulfurizing heavy oil, a directly desulfurized heavy oil obtained from a unit for directly desulfurizing heavy oil, a normal pressure residual oil, and a deasphalted oil obtained from a unit for deasphalting heavy oil.

The catalyst used in fluidized catalytic cracking is not particularly limited, and a known catalyst for fluidized catalytic cracking may be used. Examples of the catalyst for fluidized catalytic cracking include amorphous silica-alumina and zeolite.

(Dimerization Step)

The dimerization step is a step of using isobutene contained in the C4 fraction as a raw material component, and bringing a first raw material comprising the isobutene into contact with a dimerization catalyst to produce a C8 component comprising a dimer of isobutene. The first raw material in a gas form may be subjected to the dimerization reaction.

In the dimerization step, the C4 fraction may be directly used as the first raw material. In other words, the first raw material may comprise the C4 fraction, and may further comprise hydrocarbons having 4 carbon atoms other than isobutene (isobutane, normal butene, normal butane and the like).

Also; in the dimerization step, a fraction having a higher isobutene concentration may be separated from the C4 fraction for use as the first raw material. In other words, so long as the isobutene contained in the C4 fraction is contained in the first raw material, the C4 fraction other than isobutene is not necessarily required to be contained.

The first raw material may further comprise components other than hydrocarbons. The first raw material may further comprise an 1.5 inert gas as diluent, for example. Examples of the inert gas include nitrogen. Also, the first raw material may further comprise other gases such as carbon dioxide.

The isobutene concentration in the first raw material may be, for example, 1 mass % or more, or may be 5 mass % or more. The upper limit of the isobutene concentration in the first raw material is not particularly limited, and may be, for example, 100 mass %.

The dimerization catalyst may be any catalyst active in the dimerization reaction of isobutene. Examples of the dimerization catalyst include an acidic catalyst such as sulfuric acid, zeolite, solid phosphoric acid, an ion exchange resin, hydrofluoric acid, and an ionic liquid.

In the dimerization step, reaction conditions for the dimerization reaction are not particularly limited, and may be appropriately changed corresponding to the activity of the catalyst for use, etc.

The C8 component is a hydrocarbon having 8 carbon atoms produced through a reaction between 2 molecules of hydrocarbons having 4 carbon atoms (isobutene, isobutane and the like) in the first raw material. The C8 component may comprise, for example, a dimer of isobutene, a reactant of isobutene and isobutane. The C8 component may comprise, for example, at least one selected from the group consisting of 2,4,4-trimethyl-1-pentene, 2,4,4-trimethyl-2-pentene, 2,2,4-trimethylpentane, 2,5-dimethylhexane, 2,5-dimethylhexene, and 2,5-dimethylhexadiene. The C8 component obtained in the dimerization step may be one of these or may be a mixture of two or more thereof.

In the dimerization step, a first product comprising a C8 component is obtained from the first raw material. In the present embodiment, the first product may be directly used as the raw material of a cyclization step described below. Also, in the present embodiment, a part or all of components other than the C8 component (e.g., unreacted isobutene, isobutane, normal butene and isobutane) may be separated from the first product for use as the raw material in the cyclization step. Also, in the present embodiment, a part or all of the C8 component may be abstracted from the first product for use as the raw material in the cyclization step. In the case where the separated components comprise unreacted isobutene, the components may be recycled as the raw material in the dimerization step.

(Cyclization Step)

In the cyclization step, a second raw material comprising a C8 component is brought into contact with a dehydrogenation catalyst to produce p-xylene which is a product of the cyclization/dehydrogenation reaction of the C8 component. The second raw material in a gas form, may be subjected to the dehydrogenation reaction.

In the cyclization step, the first product obtained in the dimerization step may be directly used as the second raw material. In other words, the second raw material may comprise the first product, and may further comprise hydrocarbons (isobutene, isobutane, normal butene, normal butane and the like) other than the C8 component.

Also, in the cyclization step, a fraction having a higher C8 component concentration may be separated from the first product obtained in the dimerization step for use of the fraction as the second raw material. Also, in the cyclization step, a part or all of the C8 component may be abstracted from the first product obtained in the dimerization step for use as the second raw material.

The second raw material may further comprise components other than hydrocarbons. The second raw material may further comprise an inert gas as diluent, for example. Examples of the inert gas include nitrogen. Also, the second raw material gas may further comprise other gases such as carbon dioxide.

The C8 component is a hydrocarbon having 8 carbon atoms. It is desirable that the C8 component comprise a p-xylene precursor selected from the group consisting of 2,4,4-trimethyl-1-pentene, 2,4,4-trimethyl-2-pentene, 2,2,4-trimethylpentane, 2,5-dimethylhexane, 2,5-dimethylhexene, and 2,5-dimethylhexadiene. The proportion of the p-xylene precursor in the C8 component is, for example, preferably 50% or more, more preferably 80% or more, and still more preferably 95% or more.

The dehydrogenation catalyst may be any catalyst active in the cyclization/dehydrogenation reaction of the C8 component. The dehydrogenation catalyst may comprise, for example, a support and an active metal supported on the support.

As the support, an inorganic support is preferred, and an inorganic oxide support is more preferred. Also, it is preferable that the support comprises at least one element selected from the group consisting of Al, Mg, Si, Zr, Ti and Ce, and it is more preferable that the support comprises at least one element selected from the group consisting of Al, Mg and Si. As the support, an inorganic oxide support comprising Al and Mg is particularly favorably used from the perspective of efficiently obtaining p-xylene through inhibition of a side reaction.

A preferred aspect of the dehydrogenation catalyst is described as follows.

The dehydrogenation catalyst in the present aspect (hereinafter, referred to as a first dihydrogen catalyst in some cases) is a catalyst comprising supported metals comprising metal elements in the group 14 and Pt supported on a support comprising Al and metal elements in the group 2. Herein, the metal elements in the group 2 mean metal elements belonging to the group 2 in the long-period type periodic table of elements based on the specification by IUPAC (International Union of Pure and Applied Chemistry), and the metal elements in the group 14 mean metal elements belonging to the group 14 in the long-period type periodic table of elements based on the specification by IUPAC (International Union of Pure and Applied Chemistry).

The metal element in the group 2 may be, for example, at least one selected from the group consisting of beryllium (Be), magnesium (Mg), calcium (Ca), strontium (Sr) and barium (Ba). It is preferable that the metal element in the group 2 is Mg among them.

The metal element in the group 14 may be, for example, at least one selected from the group consisting of germanium (Ge), tin (Sn) and lead (Pb). It is preferable that the metal element in the group 14 is Sn among them.

The Al content in the dehydrogenation catalyst in the present aspect may be 15 mass % or more, or may be 25 mass % or more, based on the total mass of the dehydrogenation catalyst. Also, the Al content may be 40 mass % or less.

The content of the metal element in the group 2 in the dehydrogenation catalyst in the present aspect is preferably 10 mass % or more, and more preferably 13 mass % or more, based on the total mass of the dehydrogenation catalyst. The content of the metal element in the group 2 is preferably 20 mass % or less, and more preferably 16 mass % or less, based on the total mass of the dehydrogenation catalyst.

The content of the metal element in the group 14 in the dehydrogenation catalyst in the present aspect is preferably 2 mass % or more, and more preferably 4 mass % or more, based on the total mass of the dehydrogenation catalyst. The content of the metal element in the group 14 is preferably 9 mass % or less, and more preferably 6 mass % or less, based on the total mass of the dehydrogenation catalyst.

The content of Pt in the dehydrogenation catalyst in the present aspect is preferably 0.1 mass % or more, and more preferably 0.5 mass % or more, based on the total mass of the dehydrogenation catalyst. The content of Pt is preferably 5 mass % or less, and more preferably 3 mass % or less, based on the total mass of the dehydrogenation catalyst. With a Pt content of 0.1 mass % or more, the amount of platinum per amount of catalyst increases, so that the size of a reactor can be reduced. With a Pt content of 5 mass % or less, Pt particles formed on the catalyst has a size suitable for the dehydrogenation reaction and the surface area of platinum per unit platinum weight increases, so that a more efficient reaction system can be achieved.

In the dehydrogenation catalyst in the present aspect, the molar ratio of the metal elements in the group 14 to Pt (number of moles of metal elements in the group 14/number of moles of Pt) is preferably 3 or more, and more preferably 6 or more, from the perspective of further improvement of the reaction efficiency through inhibition of a side reaction. The molar ratio of the metal elements in the group 14 to Pt is preferably 15 or less, and more preferably 13 or less, from the perspective of preventing Pt particles from being excessively coated with metal elements in the group 14 to enhance the reaction efficiency.

In the dehydrogenation catalyst in the present aspect, the molar ratio of the metal elements in the group 2 to Al (number of moles of metal elements in the group 2/number of moles of Al) is preferably 0.30 or more, and more preferably 0.40 or more, from the perspective of further improvement of the reaction efficiency through inhibition of a side reaction. The molar ratio of the metal elements in the group 2 to Al is preferably 0.60 or less, and more preferably 0.55 or less, from the perspective of enhancing the dispersibility of Pt in the dehydrogenation catalyst.

The content of Al, metal elements in the group 2, metal elements in the group 14 and Pt in the dehydration catalyst can be measured under the following measurement conditions by an inductively coupled plasma atomic emission spectrometer (ICP-AES). The dehydration catalyst is subjected to alkali fusion and then dissolved with dilute hydrochloric acid to provide an aqueous solution for use in the measurement.

Apparatus: SPS-3000 manufactured by Hitachi High-Tech Science Corporation
High-frequency output: 1.2 kw
Plasma gas flow: 18 L/min
Auxiliary gas flow: 0.4 L/min
Nebulizer gas flow: 0.4 L/min The dehydrogenation catalyst in the present aspect has pores (a) having a pore diameter of 6 nm or more and 18 nm or less. The dehydrogenation catalyst may have pores having a pore diameter of 3 nm or less (hereinafter, referred to as "pore (b)"), pores having a pore diameter of more than 3 nm and less than 6 nm (hereinafter, referred to as "pore (c)"), or pores having a pore diameter of more than 18 nm (hereinafter, referred to as "pore (d)").

In the dehydrogenation catalyst in the present aspect, the proportion of the pore volume of the pore (a) may be 60% or more relative to the whole pore volume of the dehydrogenation catalyst. In the case where the proportion of the pore volume of the pore (a) is equal to or more than the proportion described above, side reactions are sufficiently inhibited and sufficient dehydrogenation activity can be obtained. The proportion of the pore volume of the pore (a) is preferably 70% or more, and more preferably 75% or more, relative to the whole pore volume of the dehydrogenation catalyst. The proportion of the pore volume of the pore (a) may be 90% or less relative to the whole pore volume of the dehydrogenation catalyst. The proportion of the pore volume of a prescribed pore can be obtained from BJH analysis of the measurement results under a nitrogen relative pressure of 0 to 0.99 by the nitrogen adsorption method.

The proportion of the pore volume of the pore (b) is preferably 10% or less, and more preferably 5% or less, relative to the whole pore volume of the dehydrogenation catalyst. The proportion of the pore volume of the pore (b) may be 1% or more relative to the whole pore volume of the dehydrogenation catalyst.

The proportion of the pore volume of the pore (c) is preferably 15% or less, and more preferably 10% or less, relative to the whole pore volume of the dehydrogenation catalyst. The proportion of the pore volume of the pore (c) may be 5% or more relative to the whole pore volume of the dehydrogenation catalyst.

The proportion of the pore volume of the pore (d) is preferably 30% or less, and more preferably 20% or less, relative to the whole pore volume of the dehydrogenation catalyst. The proportion of the pore volume of the pore (d) may be 10% or more relative to the whole pore volume of the dehydrogenation catalyst.

The proportion of the sum of the pore volumes of the pore (a) and the pore (c) is preferably 70% or more, and more preferably 80% or more, relative to the whole pore volume of the dehydrogenation catalyst. The proportion of the sum of the pore volumes of the pore (a) and the pore (c) may be 95% or less relative to the whole pore volume of the dehydrogenation catalyst.

The specific surface area of the dehydrogenation catalyst in the present aspect may be the same as the specific surface area of the support described below.

The support may be, for example, a metal oxide support comprising Al and a metal element in the group 2. The metal oxide support may be, for example, a support comprising alumina ($Al_2O_3$) and an oxide of a metal in the group 2, or may be a composite oxide of Al and a metal in the group 2. The metal oxide support may be a support comprising a composite oxide of Al and a metal element in the group 2, and at least one selected from the group consisting of alumina and an oxide of a metal element in the group 2. The composite oxide of Al and a metal in the group 2 may be, for example, $MgAl_2O_4$.

The Al content in a support may be 20 mass % or more, or may be 30 mass % or more, based on the whole mass of the support. Also, the Al content in a support may be 70 mass % or less, or may be 60 mass % or less, based on the whole mass of the support.

The content of the metal element in the group 2 in a support may be 10 mass % or more, or may be 15 mass % or more, based on the whole mass of the support. Also, the content of the metal element in the group 2 may be 30 mass % or less, or may be 20 mass % or less, based on the whole mass of the support.

The content of the composite oxide of Al and the metal element in the group 2 in a support may be 60 mass % or more, or may be 80 mass % or more, based on the whole mass of the support. The content of the composite oxide of Al and the metal element in the group 2 in a support may be 100 mass % or less, or may be 90 mass % or less, based on the whole mass of the support.

The content of alumina in a support may be 10 mass % or more, or may be 30 mass % or more, based on the whole mass of the support. The content of alumina in a support may be 90 mass % or less, or may be 80 mass % or less, based on the whole mass of the support.

The content of the oxide of the metal element in the group 2 in a support may be 15 mass % or more, or may be 25 mass % or more, based on the whole mass of the support. The content of the oxide of the metal element in the group 2 in a support may be 50 mass % or less, or may be 35 mass % or less, based on the whole mass of the support.

The support may comprise other metal elements other than Al and a metal element in the group 2. The other metal elements may be, for example, at least one selected from the group consisting of Li, Na, K, Zn, Fe, In, Se, Sb, Ni and Ga. The other metal elements may be present as an oxide, or may be present as a composite oxide of Al and at least one selected from the group consisting of metal elements in the group 2.

The support may have the pore (a), the pore (b), the pore (c), or the pore (d).

The proportions of the pore volume of the pore (a), the pore (b), the pore (c) and the pore (d) in a support may be, for example, at the same level of the proportions of the pore volume each in the dehydrogenation catalyst described above. Consequently, a dehydrogenation catalyst having a proportion of the pore volume in the favorable range described above can be easily obtained.

It is preferable that the acidity of a support is around neutral from the perspective of inhibiting side reactions. Herein, the acidity of a support is typically determined based on the pH of the support dispersed in water. In other words, the acidity of a support in the present specification can be represented by the pH of a suspension with 1 mass % of the support suspended. The acidity of the support may be preferably at a pH of 5.0 to 9.0, more preferably at a pH of 6.0 to 8.0.

The specific surface area of a support may be, for example, 50 $m^2/g$ or more, and preferably 80 $m^2/g$ or more. The resulting effect is that the dispersibility of Pt supported can be easily enhanced. Also, the specific surface area of a support may be, for example, 300 $m^2/g$ or less, and preferably 200 $m^2/g$ or less. A support having such a specific surface area tends to have no micro pores that easily collapse when the support is fired at high temperature. Consequently, the dispersibility of Pt supported tends to be enhanced. The specific surface area of a support is measured by a BET specific surface area meter using nitrogen adsorption method.

The method for preparing a support is not specifically limited, and may be, for example, a sol-gel method, a coprecipitation method, a hydrothermal synthesis method, an impregnation method, or a solid phase synthesis method. An impregnation method is preferred from the perspective of easily controlling the proportion of the pore volume of the pore (a) within the favorable proportion described above.

An aspect of the impregnation method is described below as an example of the method for preparing a support. First, to a solution in which a precursor of a first metal element (for example, a metal element in the group 2) is dissolved in a solvent, a precursor of a support comprising a second metal element (for example, Al) is added, and the solution is stirred. The solvent is then removed under reduced pressure, and a solid thus obtained is dried. The solid after drying is fired to produce a support comprising the first metal element and the second metal element. In the aspect, the content of the target metal element contained in the support can be adjusted with the concentration of the metal element in the solution containing the target metal element, the amount of the solution used, and the like.

The metal precursor may be, for example, a salt or a complex comprising a metal element. The salt comprising a metal element may be, for example, an inorganic salt, a salt of an organic acid, or a hydrate thereof. The inorganic salt may be, for example, a sulfate, a nitrate, a chloride, a phosphate, or a carbonate. The organic salt may be, for example, an acetate, or an oxalate. The complex comprising a metal element may be, for example, an alkoxide complex, or an amine complex.

Examples of the solvent in which a metal precursor is dissolved include hydrochloric acid, nitric acid, aqueous ammonia, ethanol, chloroform and acetone.

Examples of the precursor of a support comprising a second metal element include alumina (for example, γ-alumina). The precursor of a support can be prepared by, for example, a sol-gel method, a coprecipitation method, a hydrothermal synthesis method. A commercially available alumina may be used as the precursor of a support.

The precursor of a support may have the pore (a) described above. The proportion of the pore volume of the pore (a) in the precursor of a support may be 50% or more, may be 60% or more, or may be 70% or more, relative to the whole pore volume of the precursor of a support. In this case, the proportion of the pore volume of the pore (a) in the dehydrogenation catalyst can be easily controlled within the favorable proportion described above. The proportion of the pore volume of the pore (a) may be 90% or less. The proportion of the pore volume of a prescribed pore in the precursor of a support is measured by the same method as in the measurement of the proportion of the pore volume of a prescribed pore diameter in the dehydrogenation catalyst.

The firing may be performed, for example, under an air atmosphere or an oxygen atmosphere. The firing may be performed in one step, or in multi steps including two or more steps. The firing temperature may be any temperature at which the metal precursor can be decomposed, and may be, for example, 200 to 1000° C., or may be 400 to 800° C. When a multi-step firing is performed, at least one step of the steps is required to be at the above firing temperature. The firing temperature in other steps may be, for example, in the same range as described above, or may be 100 to 200° C.

As the conditions during stirring, for example, the stirring temperature may be set at 0 to 60° C., and the stirring time at 10 minutes to 24 hours. As the conditions during drying, for example, the drying temperature may be set at 100 to 250° C., and the drying time at 3 hours to 24 hours.

In the dehydrogenation catalyst in the present aspect, a supported metal comprising a metal element in the group 14 and Pt is supported. The supported metal may be supported as an oxide on a support, or may be supported as a simple metal on a support.

On a support, a metal element other than the metal element in the group 14 and Pt may be supported. Examples of the other metal elements are the same as the examples of the other metal elements which the support can comprise. The other metal elements may be supported as a simple metal, may be supported as an oxide, or may be supported as a composite oxide of at least one selected from the group consisting of metal elements in the group 14 and Pt.

The amount of the metal element in the group 14 supported on a support is preferably 1.5 parts by mass or more, more preferably 3 parts by mass or more, relative to 100 parts by mass of the support. Also, the amount of the metal element in the group 14 supported on a support may be 10 parts by mass or less, or may be 8 parts by mass or less, relative to 100 parts by mass of the support. In the case where the amount of the metal element in the group 14 is in the above range, the deterioration of the catalyst tends to be further inhibited to maintain the high activity for a longer period.

The amount of Pt supported on a support is preferably 0.1 parts by mass or more, more preferably 0.5 parts by mass or more, relative to 100 parts by mass of the support. Also, the amount of Pt supported on a support may be 5 parts by mass or less, or may be 3 parts by mass or less, relative to 100 parts by mass of the support. With such an amount of Pt, Pt particles formed on the catalyst has a size suitable for the dehydrogenation reaction and the surface area of platinum per unit platinum weight increases, so that a more efficient reaction system can be achieved. Also, with such an amount of Pt, a high activity can be maintained for a longer period, while the catalyst cost is suppressed.

The method for supporting a metal on a support is not particularly limited, and examples of the method include an impregnation method, a precipitation method, a coprecipitation method, a kneading method, an ion exchange method, and a pore filing method.

An aspect of the method for supporting a metal on a support is described as follows. First, to a solution in which the precursor of a target metal (supported metal) is dissolved in a solvent (for example, an alcohol), a support is added, and the solution is stirred. The solvent is then removed under reduced pressure, and a solid thus obtained is dried. The solid after drying is fired, so that the target metal can be supported on the support.

In the supporting method described above, the precursor of the supported metal may be, for example, a salt or a complex which comprises the metal element. The salt comprising the metal element may be, for example, an inorganic salt, a salt of an organic acid, or a hydrate thereof. The inorganic salt may be, for example, a sulfate, a nitrate, a chloride, a phosphate, or a carbonate. The salt of an organic acid may be, for example, an acetate, or an oxalate. The complex comprising the metal element may be, for example, an alkoxide complex, or an amine complex.

As the conditions during stirring, for example, the stirring temperature may be set at 0 to 60° C., and the stirring time at 10 minutes to 24 hours. Also, as the conditions during drying, for example, the drying temperature may be set at 100 to 250° C., and the drying time at 3 hours to 24 hours.

The firing may be performed, for example, under an air atmosphere or an oxygen atmosphere. The firing may be performed in one step, or in multi steps including two or more steps. The firing temperature may be any temperature at which the precursor of the supported metal can be decomposed, and may be, for example, 200 to 1000° C., or may be 400 to 800° C. When a multi-step firing is performed, at least one step of the steps is required to be at the above firing temperature. The firing temperature in other steps may be, for example, in the same range as described above, or may be 100 to 200° C.

The dispersibility of Pt in the dehydrogenation catalyst in the present aspect may be 10% or more, preferably 15% or more. A dehydrogenation catalyst having such a dispersibility of Pt further inhibits a side reaction, so that the high activity tends to be maintained for a longer period. The dispersibility of Pt is measured by a method for measuring dispersibility of metal using CO as adsorbed species, with the following apparatus and the conditions.

Apparatus: apparatus for measuring dispersibility of metal R-6011, manufactured by Ohkurariken Co., Ltd.
Gas flow rate: 30 mL/min (helium, hydrogen)
Amount of sample: about 0.1 g (precisely weighed down to the fourth decimal place)
Pretreatment: Under a hydrogen stream, the temperature is raised to 400° C. over a period of 1 hour, and a reduction treatment is performed at 400° C. for 60 minutes. The gas is then switched from hydrogen to helium for purging at 400° C. for 30 minutes, and the temperature is lowered to room temperature under a helium stream. After the detector is stabilized at room temperature, the CO pulse is performed.
Measurement conditions: Under a helium gas flow at normal pressure, carbon monoxide is pulse-injected by 0.0929 $cm^3$ each at room temperature (27° C.) to measure the amount adsorbed. The adsorption step is repeated until the adsorption is saturated (a minimum of 3 and a maximum of 15). From the measured amount adsorbed, the dispersibility is obtained.

The dehydrogenation catalyst may be a dehydrogenation catalyst other than the ones described above. Examples of the preferred dehydrogenation catalyst other than the above include a catalyst using Cr as the supported metal in the above aspect.

A dehydrogenation catalyst may be molded by a method such as extrusion and tablet pressing.

A dehydrogenation catalyst may contain a molding aid within a range that causes no impairment to the physical properties of the catalyst or the performance of the catalyst, from the perspective of improving the molding properties in a molding step. The molding aid may be, for example, at least one selected from the group consisting of a thickener, a surfactant, a humectant, a plasticizer, and a binder raw material. The molding step of molding a dehydrogenation catalyst may be performed in an appropriate stage in the manufacturing process of the dehydrogenation catalyst, considering the reactivity of the molding aid.

The shape of the dehydrogenation catalyst molded is not particularly limited, and can be appropriately selected corresponding to the embodiment of the use of the catalyst. For example, the shape of the dehydrogenation catalyst may be a pellet form, a granular form, a honeycomb form, a sponge form, or the like.

A dehydrogenation catalyst subjected to a reduction treatment as pretreatment may be used. The reduction treatment can be performed, for example, by retaining a dehydrogenation catalyst at 40 to 600° C. under an atmosphere of reducing gas. The retention time may be, for example, 0.05 to 24 hours. The reducing gas may be, for example, hydrogen, or carbon monoxide.

Use of the dehydrogenation catalyst subjected to a reduction treatment enables an initial induction period of the dehydrogenation reaction to be shortened. The induction period of the initial reaction refers to a state of the catalyst having low activity, with very few active metals contained in the catalyst being reduced to an activated state.

Subsequently, the reaction conditions in the cyclization step, etc. are described in detail.

The cyclization step is a step of causing a second raw material to react with a dehydrogenation catalyst such that the cyclization/dehydrogenation reaction of C8 component are performed to produce p-xylene.

The cyclization step may be performed, for example, by passing a second raw material through a reactor filled with a dehydrogenation catalyst. As the reactor, various reactors for use in gas-phase reactions with a solid catalyst may be used. Examples of the reactor include a fixed bed reactor, a radial flow reactor, and a tube reactor.

The reaction type of the cyclization/dehydrogenation reaction may be, for example, a fixed bed type, a moving bed type, or a fluidized bed type. Among them, a fixed bed type is preferred from the perspective of equipment cost.

The reaction temperature of the cyclization/dehydrogenation reaction, i.e., the temperature in the reactor, may be 300 to 800° C., may be 400 to 700° C., or may be 500 to 650° C., from the perspective of the reaction efficiency. With a reaction temperature of 300° C. or more, the output of p-xylene tends to be further increased. With a reaction temperature of 800° C. or less, the coking rate does not excessively increase, so that the high activity of the dehydrogenation catalyst tends to be maintained for a longer period.

The reaction pressure, i.e., the atmospheric pressure in a reactor, may be 0.01 to 1 MPa, may be 0.05 to 0.8 MPa, or may be 0.1 to 0.5 MPa. With a reaction pressure in the above range, the dehydrogenation reaction easily proceeds, so that further excellent reaction efficiency tends to be obtained.

In the case where the cyclization step is performed by a continuous reaction with the second raw material continuously supplied, the weight hourly space velocity (hereinafter, referred to as "WHSV") may be, for example, 0.1 $h^{-1}$ or more, or may be 0.5 $h^{-1}$ or more. Also, the WHSV may be 20 $h^{-1}$ or less, or may be 10 $h^{-1}$ or less. Herein, WHSV is the ratio (F/W) of the supply rate (supply/hour) of the raw material gas (second raw material) F to the mass of the dehydrogenation catalyst W. With a WHSV of 0.1 $h^{-1}$ or more, the reactor size can be further reduced. With a WHSV of 20 $h^{-1}$ or less, the conversion ratio of the C8 component can be further increased. The amount of the raw material gas and the catalyst for use may be appropriately selected in a further favorable range corresponding to the reaction conditions, the activity of the catalyst, and the like, and the WHSV is not limited to the range described above.

In the cyclization step, a second product comprising p-xylene is obtained from the second raw material. The production method according to the present embodiment may further comprise an isolation step of isolating p-xylene from the second product. The second product may further comprise hydrocarbons other than p-xylene, and the hydrocarbons may be recycled as raw material in the dimerization step or the cyclization step. For example, the second product may comprise isobutene, isobutane, and the like as a by-product of the cyclization/dehydrogenation reaction. Recycling of isobutene in the second product as raw material in the dimerization step allows the yield of p-xylene to be increased. Also, recycling of isobutane in the second product as raw material in the dimerization step or the cyclization step causes the conversion of isobutane to isobutene with the dehydrogenation catalyst in the cyclization step. Further recycling of isobutene derived from isobutane as raw material in the dimerization step allows the yield of p-xylene to be further increased.

Specific aspects of the production method according to the present embodiment are exemplified as follows.

(1) First Aspect

The production method according to the first aspect further comprises a first separation step of obtaining a fraction (A) comprising isobutene and isobutane and a fraction (B) comprising normal butene and normal butane from a C4 fraction, and a second separation step of obtaining a fraction (A-1) comprising isobutene and a fraction (A-2) comprising isobutane, and a first raw material comprising the fraction (A-1) is used in the dimerization step.

The first separation step can be performed, for example, by reactive distillation, superfractionation, membrane separation, or TBA dehydration (a method including hydrating isobutene to produce tert-butyl alcohol (TBA), separating TBA from other components, and dehydrating TBA to produce isobutene), and reactive distillation is preferred among them, from the perspective of excellence in economic efficiency.

The catalyst and conditions in the reactive distillation are not particularly limited, and a known catalyst and conditions may be employed.

The second separation step can be performed, for example, by atmospheric distillation, vacuum distillation, membrane separation, or TBA dehydration, and TBA dehydration is preferred among them, from the perspective of excellence in economic efficiency.

The production method according to the first aspect may further comprise a butadiene production step of bringing a third raw material comprising the fraction (B) into contact with a dehydrogenation catalyst to produce butadiene. Such a step enables butadiene useful as a chemical to be produced in addition to p-xylene, so that C4 fraction can be more effectively used.

The dehydrogenation catalyst used in the butadiene production step may be any catalyst active in the dehydrogenation reaction of normal butane and/or normal butene, and examples thereof include the same catalysts as the dehydrogenation catalysts used in the cyclization step. The dehydrogenation catalyst used in the butadiene production step may be the same dehydrogenation catalyst used in the cyclization step or may be different therefrom.

In the butadiene production step, for example, the dehydrogenation catalyst according to the preferred aspect described above (first dehydrogenation catalyst) and another catalyst may be used together.

For example, in the butadiene production step, a stage subsequent to that of a first dihydrogen catalyst in a reactor may be further filled with a solid catalyst (second dehydrogenation catalyst) which catalyzes a dehydrogenation reaction from an olefin to a conjugated diene. Since the first dehydrogenation catalyst has excellent activity to the dehydrogenation reaction from an alkane to an olefin, filling a stage subsequent to that of the first dehydrogenation catalyst with the second dehydrogenation catalyst can enhance the yield of butadiene.

Also, the butadiene production step may be a step of bringing a third raw material into contact with the first dehydrogenation catalyst to produce a third product, and further bringing the third product into contact with a second dehydrogenation catalyst to produce a fourth product comprising butadiene. Such a step enables butadiene to be produced with a higher yield.

As long as the second dehydrogenation catalyst is a catalyst for dehydrogenation reaction of olefins, the catalyst is not particularly limited. As the second dehydrogenation catalyst, for example, $Pt/Al_2O_3$ catalysts which are widely used as catalyst of a simple dehydrogenation reaction, and Bi—Mo catalysts which are widely used as catalyst of an oxidative dehydrogenation reaction can be used.

(2) Second Aspect

The production method according to the second aspect further comprises a first separation step of obtaining a fraction (A) comprising isobutene and isobutane and a fraction (B) comprising normal butene and normal butane from a C4 fraction, and a first raw material comprising the fraction (A) is used in the dimerization step.

In the second aspect, since the first raw material comprises isobutane, the first product produced in the dimerization step comprises unreacted isobutane. In the second aspect, isobutane contained in the first product may be subjected to the cyclization step together with the C8 component. As a result, isobutane causes a reaction with the dehydrogenation catalyst in the cyclization step to form isobutene. Isobutene thus formed is contained in the second product in the cyclization step, and recycled in the dimerization step to increase the yield of p-xylene.

In the second aspect, a butadiene production step of bringing a third raw material comprising the fraction (B) into contact with the dehydrogenation catalyst to produce butadiene may be further provided. Such a step enables butadiene useful as a chemical to be produced in addition to p-xylene, so that the C4 fraction can be more effectively used.

Also, in the second aspect, an isomerization step of bringing a third raw material comprising the fraction (B) into contact with an isomerization catalyst to produce isobutene and isobutane may be further provided. Isobutene and isobutane produced by such a step can be used as raw material in the dimerization step, so that the yield of p-xylene can be further increased.

The isomerization catalyst may be any catalyst which can isomerize normal butane and normal butene to isobutane and isobutene, and a known isomerization catalyst may be used. Examples of the isomerization catalyst include zeolite, a solid ultrastrong acid and silica-alumina, and among them, a solid ultrastrong acid can be favorably used from the perspective of excellence in the reactivity.

(3) Third Aspect

In the production method according to the third aspect, the first raw material comprising isobutene and normal butene is used in the dimerization step. In the third aspect, the C4 fraction comprising isobutene and normal butene may be directly used as the first raw material.

In the third aspect, since the first raw material comprises normal butene, the first product obtained in the dimerization step comprises unreacted normal butene. In the third aspect, normal butene contained in the first product may be subjected to the cyclization step together with the C8 component. Thereby, normal butene is dehydrogenated with the dehydrogenation catalyst in the cyclization step to form butadiene. As a result, p-xylene and butadiene useful as chemicals can be obtained at the same time.

In the third aspect, the reactor in the cyclization step may be further filled with a catalyst (for example, the second dehydrogenation catalyst described above) other than the dehydrogenation catalyst according to the preferred aspect described above (the first dehydrogenation catalyst).

Although preferred embodiments of the present invention are described above, the present invention is not limited to the embodiments.

EXAMPLES

The present invention is described in detail with reference to Examples as follows, though the present invention is not limited to Examples.

Example 1

Preparation of Catalyst A-1

As a precursor of a support, 6.0 g of γ-alumina classified to a size of 0.5 to 1 mm (NEOBEAD GB-13, manufactured by Mizusawa Industrial Chemicals, Ltd., pH of a suspension thereof in water at a concentration of 1 mass %: 7.9) was prepared. The precursor of a support and a solution of 15.1 g of $Mg(NO_3)_2 \cdot 6H_2O$ dissolved in 45 ml of water were mixed. The resulting mixture was stirred at 40° C. under 0.015 MPaA for 30 minutes with a rotary evaporator, and then further stirred at 40° C. under atmospheric pressure for 30 minutes. Water was then removed from the mixture under reduced pressure, while stirring the mixture. The resulting solid was dried overnight in an oven at 130° C. Subsequently, the solid after drying was fired in two steps, at 550° C. for 3 hours and at 800° C. for 3 hours, under an air stream to produce a support A-1 comprising $MgAl_2O_4$.

Using a nitric acid solution of diamine dinitro platinum (II) ($[Pt(NH_3)_2(NO_2)_2]/HNO_3$, manufactured by Tanaka Kikinzoku Kogyo K.K.), 10.0 g of the support A-1 was impregnated with platinum so as to have an amount of platinum supported of about 1 mass %, dried at 130° C. overnight, and fired at 550° C. for 3 hours. Subsequently, the impregnated support was mixed with an aqueous solution of 0.82 g of sodium stannate ($Na_2SnO_2 \cdot 3H_2O$, manufactured by Showa Kako Corp.) dissolved in about 30 ml of water, and water was removed at about 50° C. by an evaporator. The impregnated support was then dried at 130° C. overnight and fired at 550° C. for 3 hours to produce a catalyst A-1. Through ICP analysis of the resulting catalyst A-1, it was found that the amount of Pt supported was 0.92 mass %, and the amount of Sn supported was 3.0 mass %.

<Production of p-Xylene>

The C4 fraction obtained by processing Middle East crude oil with a fluidized catalytic cracking apparatus was fractionated in a reactive distillation apparatus to produce isobutane and isobutene from the column top and normal butane and normal butene from the column bottom, respectively. In the column top gas, the isobutane content was 76 mass %, and the isobutene content was 24 mass %. Using a fixed-bed flow reactor, the column top gas was processed with AMBERLYST 35, i.e., a strong acid ion exchange resin, under conditions at 120° C., under atmospheric pressure, with a WHSV of 50 h$^{-1}$, so that a product (first product) comprising 76 mass % of isobutane, 23 mass % of 2,4,4-trimethylpentene, and 1 mass % of other components was obtained.

Subsequently, using a fixed-bed flow reactor, the first product as raw material was subjected to a cyclization/dehydrogenation reaction under conditions at 550° C., under atmospheric pressure, with a WHSV of 20 h$^{-1}$. The catalyst A-1 was used as catalyst. A reaction product after 9 hours from the reaction initiation was analyzed to determine the conversion ratio of 2,4,4-trimethylpentene, the yield of para-xylene, and the para-xylene fraction in xylene. The results obtained are shown in Table 1. The yield of para-xylene shown in Table 1 represents a yield relative to 2,4,4-trimethylpentene.

Example 2

Preparation of Catalyst A-2

A support A-1 was prepared by the same method as in Example 1. Subsequently, using an aqueous solution of chromium nitrate ([Cr(NO$_3$)$_2$]6H$_3$O, manufactured by Wako Pure Chemical Industries, Ltd.), 10.0 g of the support A-1 was impregnated with chromium so as to have an amount of chromium supported of about 5 mass %, dried at 130° C. overnight, and fired at 550° C. for 3 hours to produce a catalyst A-2.

<Production of p-Xylene>

The cyclization/dehydrogenation reaction was performed in the same manner as in Example 1 except that the catalyst A-2 was used as catalyst, and a reaction product after 9 hours from the reaction initiation was analyzed. The analysis results are as shown in Table 1.

Example 3

Preparation of Catalyst A-3

Using an aqueous solution of chromium nitrate ([Cr(NO$_3$)$_2$]6H$_3$O, manufactured by Wako Pure Chemical Industries, Ltd.), 6.0 g of γ-alumina (NEOBEAD GB-13, manufactured by Mizusawa Industrial Chemicals, Ltd., pH of a suspension thereof in water at a concentration of 1 mass %: 7.9) was impregnated with chromium so as to have an amount of chromium supported of about 5 mass %, dried at 130° C. overnight, and fired at 550° C. for 3 hours to produce a catalyst A-3.

<Production of p-Xylene>

The cyclization/dehydrogenation reaction was performed in the same manner as in Example 1 except that the catalyst A-3 was used as catalyst, and a reaction product after 9 hours from the reaction initiation was analyzed. The analysis results are as shown in Table 1.

The results in Examples 1 to 3 are shown in Table 1. In Table 1, the TMP conversion ratio represents the conversion ratio of 2,4,4-trimethylpentene, the yield of para-xylene represents a yield of para-xylene relative to 2,4,4-trimethylpentene, and the para-xylene fraction represents a proportion of para-xylene in xylenes in a product.

TABLE 1

|  | Example 1 | Example 2 | Example 3 |
|---|---|---|---|
| TMP conversion ratio (mass %) | 85.3 | 80.3 | 90.8 |
| Yield of para-xylene (mass %) | 10.1 | 5.5 | 6.0 |
| para-xylene fraction (mass %) | 94.3 | 92.8 | 90.6 |

As shown in Table 1, in each Examples, para-xylene can be efficiently produced from the C4 fraction in the product of fluidized catalytic cracking. Also, in comparison with Examples 2 and 3, a higher yield of para-xylene was achieved with a high para-xylene fraction in Example 1.

The invention claimed is:

1. A method for producing p-xylene, comprising:
   providing a C4 fraction comprising at least isobutene as a product formed by fluidized catalytic cracking of a heavy oil fraction;
   bringing a first raw material comprising the isobutene into contact with a dimerization catalyst to produce a C8 component comprising a dimer of the isobutene; and
   bringing a second raw material comprising the C8 component into contact with a dehydrogenation catalyst to produce p-xylene through a cyclization/dehydrogenation reaction of the C8 component, wherein
   the dehydrogenation catalyst comprises supported metals comprising
     at least one metal element in group 14 and
     Pt
   supported on a support comprising
     Al and
     at least one metal element in group 2, and
   the molar ratio of the at least one metal element in group 14 to Pt (number of moles of at least one metal element in group 14/number of moles of Pt) in the dehydrogenation catalyst is from 5.4 to 15, and
   the content of the at least one metal element in group 14 in the dehydrogenation catalyst is 4 mass % or more based on the total mass of the dehydrogenation catalyst.

2. The method according to claim 1, wherein the C4 fraction further comprises isobutane, normal butene and normal butane.

3. The method according to claim 2, further comprising obtaining a fraction (A) comprising the isobutene and the isobutane and a fraction (B) comprising the normal butene and the normal butane from the C4 fraction.

4. The method according to claim 3, wherein the first raw material comprises the fraction (A).

5. The method according to claim 3, further comprising obtaining a fraction comprising isobutene (A-1) and a fraction comprising isobutane (A-2) from the fraction (A).

6. The method according to claim 5, wherein the first raw material comprises the fraction (A-1).

7. The method according to claim 3, further comprising bringing a third raw material comprising the fraction (B) into contact with a dehydrogenation catalyst to produce butadiene.

8. The method according to claim 3, further comprising bringing a third raw material comprising the fraction (B) into contact with an isomerization catalyst to produce isobutene and isobutane.

9. The method according to claim 8, wherein the produced isobutene is used as a part of the first raw material.

10. The method according to claim 1, wherein the dimerization catalyst comprises at least one acidic catalyst selected from the group consisting of sulfuric acid, zeolite, solid phosphoric acid, hydrofluoric acid, an ionic liquid, and an ion exchange resin.

11. The method according to claim 1, wherein the dehydrogenation catalyst comprises an inorganic oxide support comprising Al and Mg, and an active metal supported on the inorganic oxide support.

12. The method according to claim 11, wherein the active metal comprises Pt and Sn.

* * * * *